United States Patent [19]
Vial et al.

[11] Patent Number: 6,096,788
[45] Date of Patent: Aug. 1, 2000

[54] ANTIMALARIA AND ANTIBABESIOSIS AGENTS AND PHARMACEUTICAL COMPOSITIONS CONTAINING SUCH AGENTS

[75] Inventors: Henri Vial; Michele Calas, both of Montpellier; Marie-Laure Ancelin, Saint Jean de Cuculles; Louis Giral, Montpellier, all of France

[73] Assignee: Virbac S.A., Carros, France

[21] Appl. No.: 09/240,627

[22] Filed: Feb. 1, 1999

Related U.S. Application Data

[63] Continuation of application No. PCT/FR97/01336, Jul. 17, 1997.

[30] Foreign Application Priority Data

Jul. 31, 1996 [FR] France .................................. 96/09678

[51] Int. Cl.$^7$ .................................................. A01N 43/40
[52] U.S. Cl. ................................................................ 514/895
[58] Field of Search ............................................. 514/895

[56] References Cited

FOREIGN PATENT DOCUMENTS

WO 96/11910  4/1996  WIPO .

OTHER PUBLICATIONS

M.L. Ancelin et al., "Inhibitors of choline transport into Plasmedium–infected erythrocytes are effective antiplasmodial compounds in vitro", pp. 4068–4071, Biochemical Pharmacology, vol. 34, No. 22, Jun. 27, 1985.

M.L. Ancelin et al., "Quaternary Ammonium Compounds Efficiently Inhibit Plasmodium falciparum Growth In Vitro by Impairment of Choline Transport", pp. 814–820, Antimicrobial Agents and Chemotherapy, vol. 29, No. 5, May 1986.

J.T. Holden et al., "Inhibition of High–Affinity Choline Transport in Rat Striatal Synaptosomes by Alkyl Bisquaternary Ammonium Compounds", pp. 19–27, Molecular Pharmacology, vol. 11, No. 1, Jul. 30, 1974.

Primary Examiner—Terressa M. Boykin

[57] ABSTRACT

The invention concerns pharmaceutical compositions with antimalaria and antibabesiosis activity, the active substances of these compositions and their use for formulating antimalaria drugs.

25 Claims, 6 Drawing Sheets

ANTIMALARIA AND ANTIBABESIOSIS AGENTS AND PHARMACEUTICAL COMPOSITIONS CONTAINING SUCH AGENTS

This application is a continuation of international application PCT/FR97/01336 filed Jul. 17, 1997, which designated the United States.

FIELD OF THE INVENTION

The invention concerns pharmaceutical compositions with antimalaria and antibabesiosis activity as well as the principal active substance of these compositions and their use in formulating antimalaria drugs.

BACKGROUND OF THE INVENTION

Malaria remains one of the most important parasitic diseases in the tropics. In endemic zones, malaria is an integral part of the environment and comprises one of the most powerful deterrents to the development of vast geographical areas. In such zones, all inhabitants are infected from birth to death, several times a year (up to 1,000 times in Congo), and only survive because of defense mechanisms acquired during the first years of life. It is during these early years, especially between the age of 6 months and 2 years, that malaria causes mortality, at a rate difficult to estimate.

Today, nearly two billion human beings live in endemic areas, often in highly unfavorable conditions, and are exposed to the risk of malaria, suffering its morbid or even fatal effects, often without health care. Protecting these risk groups, which account for more than one-third of the earth's population, is a major public health challenge. Several million cases of malaria are registered each year. Most, including the most severe often fatal forms of the disease, are caused by *Plasmodium falciparum* (80% of the cases worldwide). Developed countries are not spared: the number of imported cases increases steadily due to the progression of international transportation.

Drug-resistant *Plasmodium falciparum* is now the greatest threat to the fight against malaria. Resistance appeared in the early sixties in Thailand and in Columbia, then spread, reaching Africa in 1978. Movements in populations have also played a role in the development of resistance and chloroquine-resistant *Plasmodium falciparum* is now widespread throughout the world. Resistance to the second line sulfamide/pyrimethamine combination is already widespread in chloroquine-resistant areas of Southeast Asia and South America. The current emergence of multidrug resistant strains, unresponsive to any of the available antimalaria drugs, is a major threat.

Among the currently available methods used to fight against malaria, the fight against larvae and the reduction of the source remains to be analyzed in terms of reduced case incidence. These methods do not appear to have a decisive effect on malaria. Methods based on treating homes with insecticides have several inconveniences (resistance, poor acceptance by the population, high cost, no effect in the savannah environment) while personal protection using pyrethrinoid impregnated nets is known to be effective, but subject to many limitations.

A polyvalent vaccine, fully active against the different forms of the parasite and all the types of malaria, has constantly been postponed and now appears to be far off (Walsh J, Science 1987, 235, 1319, Butcher, Parisitologie, 1989, 98, 315). For many years to come, chemotherapy will remain the necessary method for populations living in endemic zones.

More than 250,000 compounds tested in a major research effort undertaken in 1963 at the Walter Reed Center in Washington D.C. led to market approval for mefloquine (Lariam®) in 1985. Resistance to this new antimalaria drug has however been induced experimentally and cases of resistance have been reported. Of even greater concern is the cross-resistance demonstrated between mefloquine and other amino-alcohols such as quinine or new drugs currently in the experimental phase such as halofantrine marketed in 1989 (Halfan®) (J. Rieckmann, Ann. Rev. Med. 1983, 34, 321–335; D. Warhust, Drugs, 1987; 33: 50–65; Struchler, Parasitol Today 1989, 5:39–40).

Babesia, which belong to a hematozoan class comparable with Plasmodium, are particularly important animal parasites. Babesia and Plasmodium are very similar, but Babesia usually causes animal disease, mainly infecting cattle and dogs. The principal causal species are *Babesia bovis, Babesia cani, Babesia gibsoni, Babesia divergens,* and *Babesia gibemina. Babesia equi* is specifically implicated in equine disease.

The inventors have evidenced a new class of compounds with strong antiprotozoal activity, particularly antimalaria and antibabesiosis activity. In addition, this antimalaria activity exhibits a novel mechanism and could thus avoid much feared drug resistance in this therapeutic class. The concept of these compounds was guided by the demonstration that phospholipid metabolism in the malaria-infected red cell is abundant and specific. Asexual parasite proliferation occurring within the erythrocyte (the parasite phase associated with clinical signs of the disease) is accompanied by substantial phospholipid (PL) neosynthesis required for the biogenesis of Plasmodium membranes. The intraerythrocyte phospholipid level increases after malarial infection, rising to 500% when the parasite has reached its mature state.

Consequently, there is an excess of phospholipid biosynthetic metabolism in the erythrocyte after Plasmodium infection. In host mammals, mature erythrocytes are totally devoid of PL biosynthesis.

Figure 1:
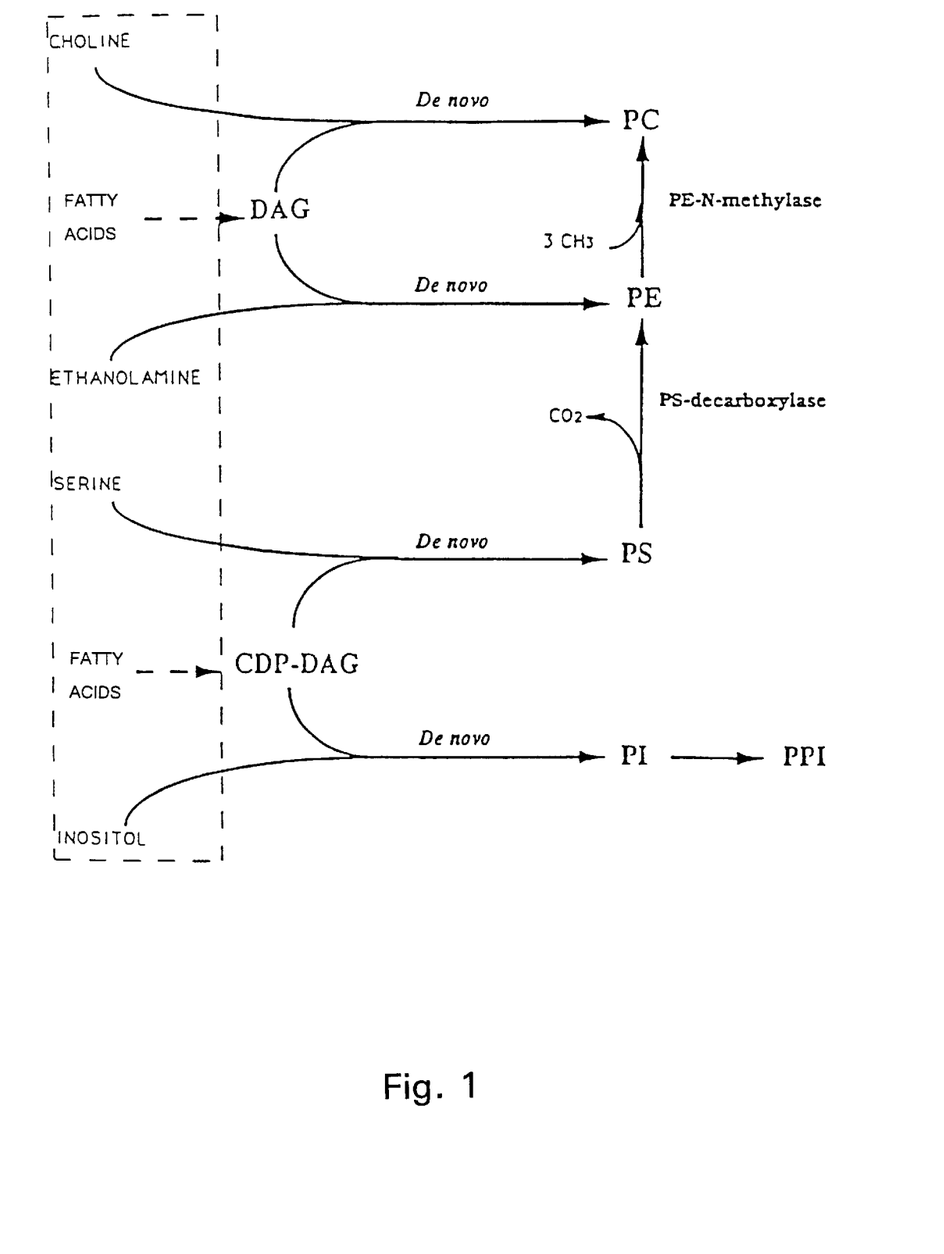
Figure 1: Schematic representation of the different biosynthesis pathways of phosphatidylethanolamine (PE) and phosphatidylcholine (PC)
Figure 2:
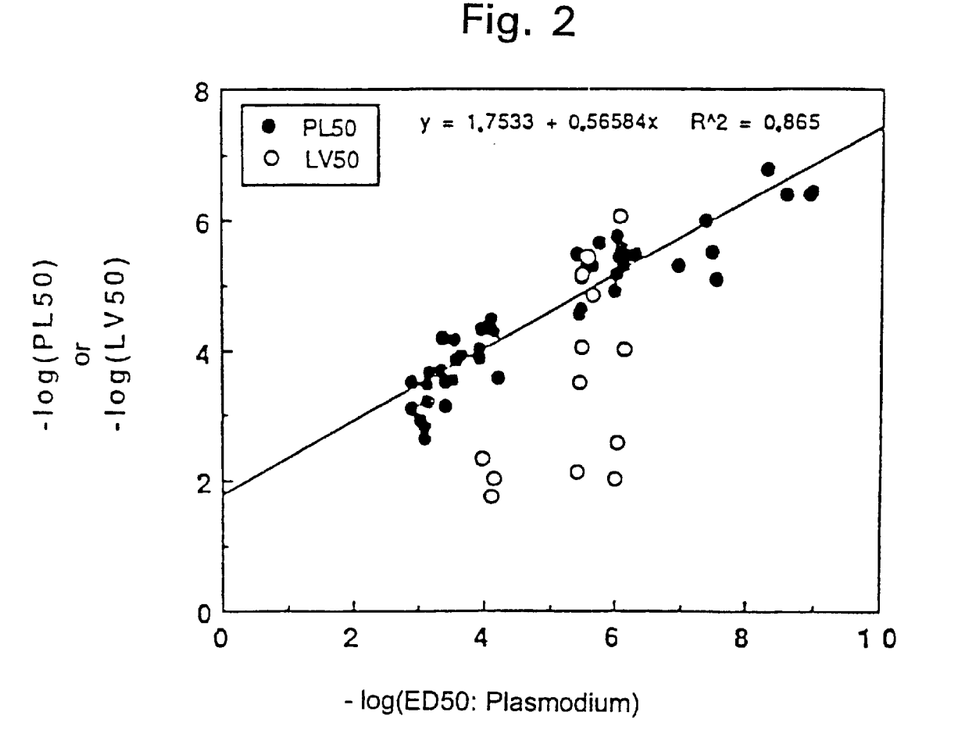
Figure 2: Correlation between antimalaria activity (ED50) and action on phospholipid metabolism (PL50) (R=0.86, which corresponds to a risk much less than 0.01%). LV50 denotes a 50% inhibition of cell viability.
Figure 3:
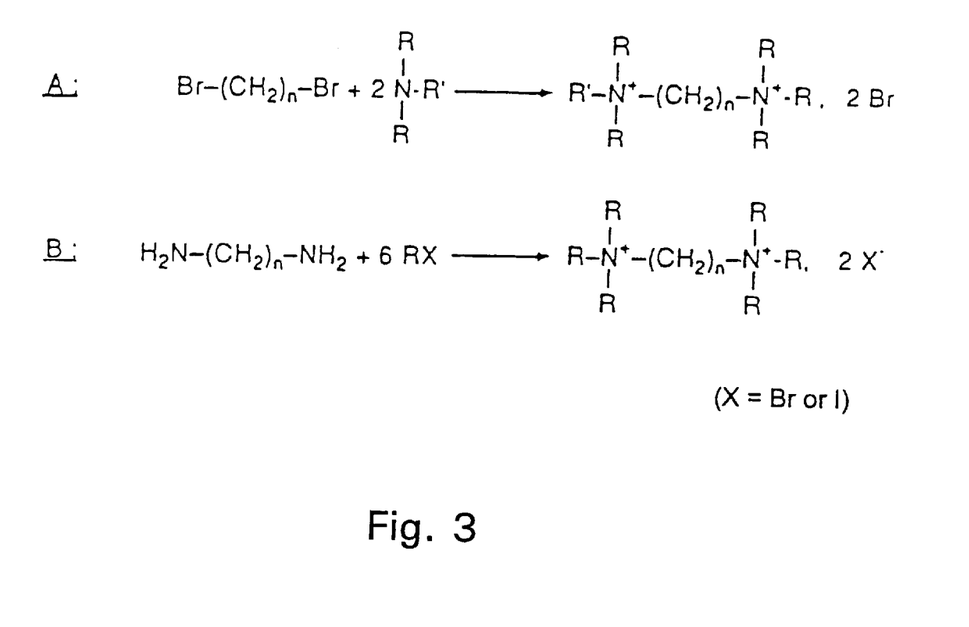
Figure 3: Synthesis pathways of quaternary bisammoniums (fonction de "n")
Figure 4:
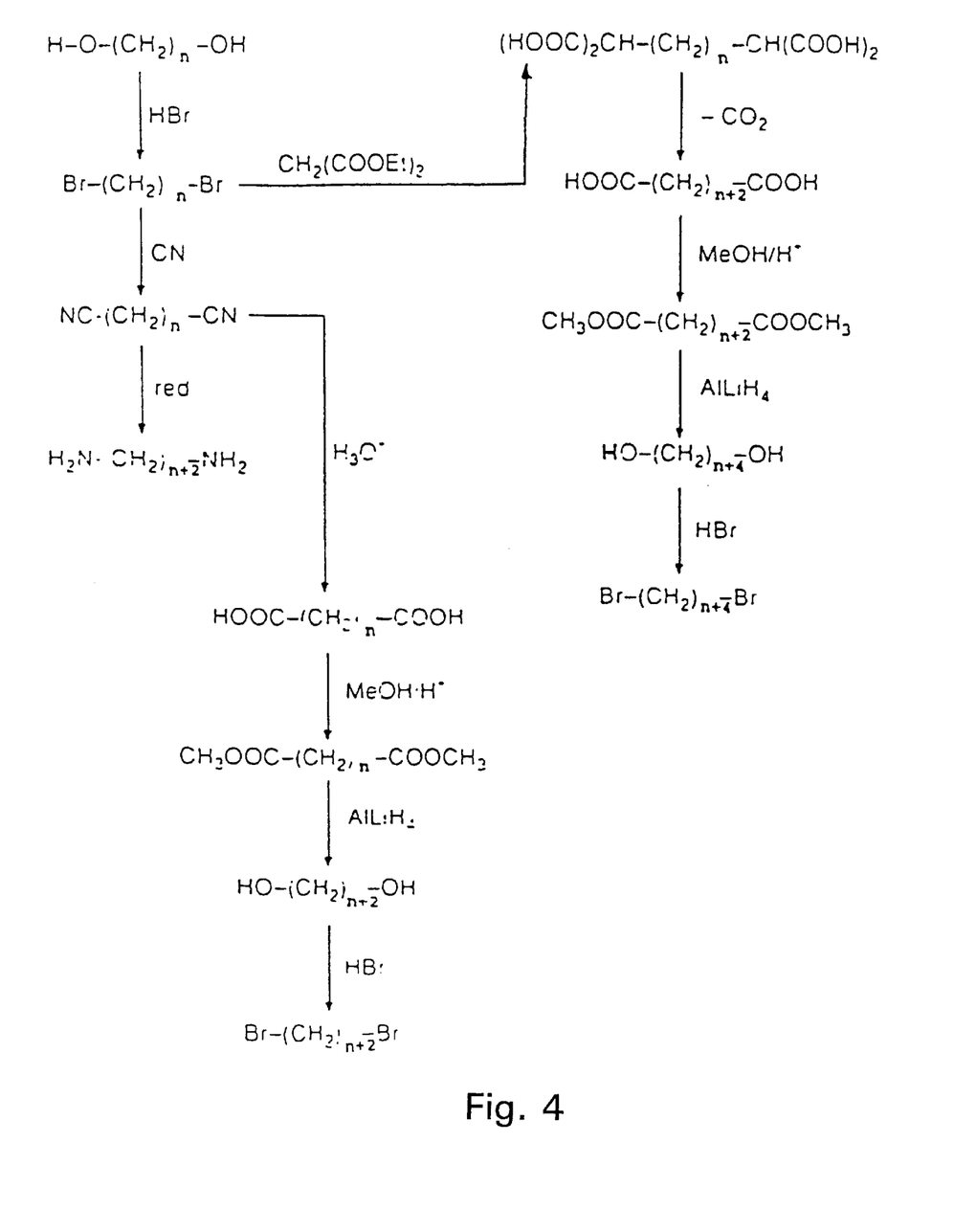
Figure 4: Reactions involving malonic syntheses.
Figure 5:
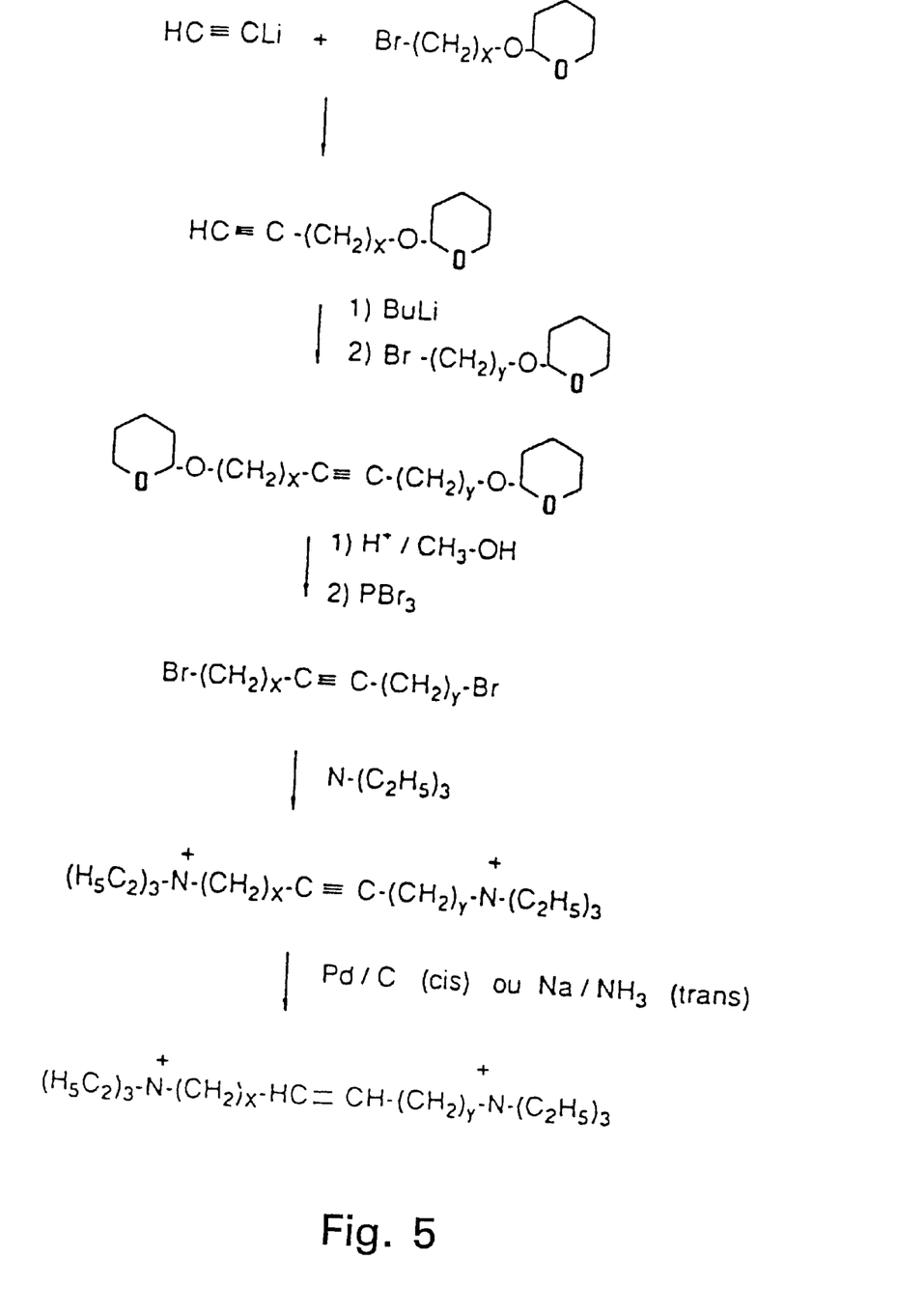
Figure 5: Synthesis of bisammonium derivatives with acetylenic and ethylenic groups.

The different biosynthesis pathways of phosphatidylethanolamines (PE) and phosphatidylcholine (PC) are schematically represented in FIG. 1. The present invention utilizes the observation that the parasite's development is blocked by substances interfering with this metabolism at doses quite below those interfering with healthy cells. Certain commercial quaternary ammoniums, with other known therapeutic activities or not, inhibit the development of *Plasmodium falciparum* but at doses incompatible with use as drugs because of side effects, notably on the cholinergic system. These quaternary salts are trimethylalkylammoniums long recognized for their effect on surface tension or their smooth muscle relaxing properties (see decamethonium, Procuran®) when given via parenteral administration. ISO-MAA (Acta Pharmacol, Toxicol 45 (5) 1979 and Biochem. Pharmacol 28 (7) 975–980) studied the action of quaternary alkyltrimethylammoniums on erythrocyte membranes in the rat and noted a protective effect on the membrane at low concentrations and a hemolytic effect at higher doses. These long-chain quaternary trimethylammoniums appear to induce changes in cell surfaces at relatively high concentrations (ISOMAA Acta Pharmacol Toxicol. 44(1) 1979 36/42). The mechanism of action, modifying the plasma membrane double lipid layer, would involve a surface tension mechanism effective at relatively high concentrations.

The series of long straight chain bis trimethylalkylammoniums have been studied, notably for their depolarizing activities on diverse cell models (Kratskin I, Gen. Pharmacol. 1980, 11(1) 119–26 and Skylarov Dokl. Akad; Nauk SSSR 1988 303 (3) 760–3). The only therapeutic activities are cholinomimetic or cholinolytic effects noted by Danilov AF (Acta Physiol; Acta Sci. Hung 1974 45 (3–4) 271–80). It is noted that all these agents affecting surface tension carry trimethylammoniums on both ends of a hydrocarbon chain generally composed of 12 methylene moities. The nitrogen atom thus carries identical, relatively small, substituents on a carbon chain usually less than 12 atoms long.

SUMMARY OF THE INVENTION

The inventors have found that, in a surprising way, diminishing the symmetry around the nitrogen atom in the quaternary biammonium components, and more generally increasing their steric bulk, strongly inhibits the choline transporter in the parasite. This dyssymmetry around the nitrogen atom is particularly notable for the smaller substituents. Conjugated with an adjustment of the length of the hydrocarbon chain carrying these two bisammonium polar heads, this surprising discovery can be used to multiply the action against Plasmodium by a factor of 1000 or even 100,000 compared with known short-chain derivatives. The optimal length of the aliphatic chain separating the two quaternary ammonium moieties influences the antiplasmodium activity. The alteration of the choline transformation into phosphatidylcholine is specific to hematozoal parasites, notably *Plasmodium falciparum* at the active concentrations used. There is no change in the other biosynthetic systems.

The invention thus concerns new chemical molecules containing two quaternary ammonium groups on the ends of a hydrocarbon chain and exerting a strong antimalaria and antibabesiosis activity. Antimalaria and antibabesiosis activity is understood as the capacity to prevent the development of the parasite within the erythrocyte and or erythrocyte invasions, and to cause the death of the parasites initially present. It is remarkable that the compounds defined in this invention have the same antimalaria activity when tested on both chloroquine-sensitive and on multidrug-resistant strains.

Thus the invention concerns a pharmaceutical composition composed of a physiologically acceptable excipient and, as its active substance, a compound defined by the general formula (1):

$$R_2-\underset{\underset{R_3}{|}}{\overset{\overset{R_1}{|}}{N^+}}----X----\underset{\underset{R'_3}{|}}{\overset{\overset{R'_1}{|}}{N^+}}-R'_2 \quad (1)$$

wherein

R1 designates a hydrocarbon group with 1 to 20 carbon atoms, and

R2 and R3 are identical or different and independently designate a hydrocarbon group with 1 to 20 carbon atoms which may have methyl or ethyl substitution groups, or halogen substitution groups such as chlorine, bromine or iodine, or trifluoromethyl, trifluoroethyl or trifluoropropyl substitution groups, where R1 is different from an ethyl group, R2 and R3 are not simultaneously methyl groups, or R1 designates a hydroxylalkyl group composed of 1 to 5 carbon atoms, where the hydroxyl groups may be etherified by a methyl, ethyl group substitution of the hydrogen atom or substituted with silicyl derivatives of the —Si(CH$_3$)$_3$ type, and R2 and R3 are identical or different from each other and designate a saturated hydrocarbon which may be substituted with halogen groups such as chlorine, bromine or iodine, or with trifluoromethyl, trlfluoroethyl or trfluoropropyl groups, or R1 designates a mono-or polyunsaturated hydrocarbon with 1 to 6 carbon atoms, and R2 and R3 are identical or different and designate a straight- or branched-chain alkyl group composed of 1 to 20 hydrocarbon units which may have methyl or ethyl substitution groups, or halogen substitution groups such as chlorine, bromine or iodine, or trifluoromethyl, trifluoroethyl or trifluoropropyl substitution groups, or R1 designates a hydrocarbon with 1 to 20 carbon atoms, and R2 and R3 form, together with nitrogen, a saturated heterogeneous cycle composed of 4 to 5 carbon atoms where one of the carbon atoms may be replaced by a silicium atom, an oxygen atom or a sulfur atom, this cycle also possibly carrrying an alkyl substitution with 1 to 3 carbon atoms which themselves may be hydroxylated, halogenated, or silicylated, where R1', R2' and R3' have the same definition as R1, R2 and R3 in the formula (1), without the restriction concerning the methyl and ethyl groups, the two polar heads being identical or not;

and where X designates a hydrocarbon which may have an alkyl substitution with 1 to 3 carbon atoms, the hydrocarbon chain having 12 to 26 carbon atoms.

Preferentially, the two polar heads of the above-described components are identical.

More specifically, the pharmaceutical compositions of the invention include an active substance defined by the general formula (1), in which the substitutions are chosen in accordance with the following combinations:

R1 designates an alkyl group chosen among the following: methyl, methylethyl, propyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl, eicosyl, and R2 and R3 are identical or different and independently designate an alkyl group chosen among the following: ethyl, propyl, isopropyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl, eicosyl which may carry methyl or ethyl substitution groups, or halogen substitution groups such as chlorine, bromine or iodine, or trifluoromethyl, trifluoroethyl or trifluoropropyl substitution groups, or R1 is a hydroxyalkyl group composed of 1 to 5 carbon atoms, namely hydroxymethyl, hydroxyethyl, hydroxypropyl, hydroxypentyl groups, where these hydroxylated groups may be etherified by substitution of a methyl, ethyl, or —Si—(CH$_3$)$_3$ group for the hydrogen atom, and R2 and R3 are identical or different from each other and can be a saturated propyl, isopropyl, butyl, sec-butyl, tert-butyl, pently, hexyl, heptyl, octyl, nonyl, decyl, undecyl, dodecyl hydrocarbon which may carry halogen substitution groups such as chlorine, bromine or iodine, or trifluoromethyl, trifluoroethyl or trifluoropropyl substitution groups, or R1 designates a mono- or polyunsaturated hydrocarbon chain of the type propenyl, propynyl, butenyl, butynyl, butadienyl, pentenyl, pentadienyl, pentynyl, hexenyl, hexadienyl, hexynyl, isoprenyl, and R2 and R3 are identical or different and designate a straight- or branched-chain alkyl composed of 1 to 20 hydrocarbon units such as methyl, ethyl, propyl, isopropyl, butyl, sec-butyl, tert-butyl, pentyl, hexyl, heptly, octyl, nonyl, decyl, undecyl, dodecyl, tridecyl, tetradecyl, pentadecyl, hexadecyl, heptadecyl, octadecyl, nonadecyl, eicosyl which may itself carry halogen substitution groups such as chlorine, bromine or iodine, or trifluoromethyl, trifluoroethyl or trifluoropropyl substitution groups, or R1 designates a methyl, methylethyl, propyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl, eicosyl group, and R2 and R3 form, together with nitrogen, a saturated heterogeneous cycle composed of 4 to 5 carbon atoms where one of the carbon atoms may be replaced by a silicium atom, an oxygen atom or a sulfur atom, this cycle also possibly carrrying a methyl, ethyl, hydroxymethyl, hydroxyethyl, methyl ethyl or hydroxypropyl substitution, or a trifluoromethyl or trifluoroethyl substitution, or a trimethylsilicyl or trimethylsilicyloxy substitution.

Preferentially, X is here a saturated hydrocarbon, preferably a straight 14 to 26 chain, and with preferably between 14 and 22, for example, 16 carbon atoms.

Avantageously, the active substance is chosen among the following compositions:

N,N' dimethyl-N,N'-diethyl-N,N'-dipropyl-1,16-hexadecanediaminium, dibromide,

N,N' dimethyl-N,N'-diethyl-N,N'-dipropyl-1,20-eicosanediaminium, dibromide,

N,N' dimethyl-N,N',N'-tetraethyl-1,16-hexadecanediaminium, dibromide,

N,N' dimethyl-N,N',N'-tetraethyl-1,18-octadecanediaminium, dibromide,

N,N' dimethyl-N,N',N'-tetraethyl-1,21-heneicosanediaminium, dibromide

-1,1'-(1-14-tetradecanediyl) bis (1-methylpyrrolidinium) dibromide,

-1,1'-(1-16-dexadecanediyl) bis (1-methylpyrrolidinium) dibromide,

-1,1'-(1-16-hexadecanediyl) bis (2-hydroxymethyl-1-methylpyrrolidinium) dibromide, N,N'-di-(2-hydroxyethyl)-N,N,N',N'-tetrapropyl-1,20-eicosanediaminium dibromide.

In case of a heterogeneous cycle with nitrogen, R1 can be a methyl, giving the following type of polar head:

N-methyl-pyrrolidinium 1-1'-1,16-hexadecanediyl bis (1-methylpyrrolidinium) dibromide, a compound carrying two of these polar heads, constitues a preferred example of the active substance of the invention.

The invention also concerns a compound used as a therapeutic agent, preferably as an antimalaria and/or antibabesiosis agent.

The invention also concerns the utilization of a compound defined by the general formula (1) to obtain an antimalaria drug, or an antibabesiosis drug:

(1)

wherein:

R1 designates a hydrocarbon group with 1 to 20 carbon atoms, and

R2 and R3 are identical or different and independently designate a hydrocarbon group with 1 to 20 carbon atoms which may have methyl or ethyl substitution groups, or halogen substitution groups such as chlorine, bromine or iodine, or trifluoromethyl, trifluoroethyl or trifluoropropyl substitution groups, or R1 designates a hydroxylalkyl group composed of 1 to 5 carbon atoms, where the hydroxyl groups may be etherified by a methyl, ethyl group substitution of the hydrogen atom or substituted with silicyl derivatives of the —Si(CH$_3$)$_3$ type, and R2 and R3 are identical or different from each other and designate a saturated hydrocarbon which may be substituted with halogen groups such as chlorine, bromine or iodine, or with trifluoromethyl, trifluoroethyl or trifluoropropyl groups, or R1 designates a mono-or polyunsaturated hydrocarbon with 1 to 6 carbon atoms, and R2 and R3 are identical or different and designate a straight- or branched-chain alkyl group composed of 1 to 20 hydrocarbon units which may have methyl or ethyl substitution groups, or halogen substitution groups such as chlorine, bromine or iodine, or trifluoromethyl, trifluoroethyl or trifluoropropyl substitution groups, or R1 designates a hydrocarbon with 1 to 20 carbon atoms, and R2 and R3 form, together with nitrogen, a saturated heterogeneous cycle composed of 4 to 5 carbon atoms where one of the carbon atoms may be replaced by a silicium atom, an oxygen atom or a sulfur atom, this cycle also possibly carrrying an alkyl substitution with 1 to 3 carbon atoms which themselves may be hydroxylated, halogenated, or silicylated, where R1', R2' and R3' have the same definition as R1, R2 and R3 in the formula (1), and where X designates a saturated hydrocarbon containing —$CH_2$— groups or cyclic groups possibly carrying an alkyl substituion with 1 to 3 carbon atoms, this hydrocarbon chain having between 11 and 26 carbon atoms.

According to this aspect of the invention, use of compounds corresponding to the above defined active agents is more specifically preferred.

The invention also concerns a procedure for preparing a pharmaceutical composition characterized by an active substance such as that defined above by the general formula (1) being combined with a physiologically acceptable excipient.

In addition this active substance can be combined with a conventional additive, such as a preservative, an antioxidant or a dilution agent.

The invention also concerns the active substances of the invention, as defined by the general formula (1) relative to the pharmaceutical compositions.

The present invention also concerns a procedure for preparing the described compounds. The compounds designated by (1) may be prepared according to known techniques. These techniques Include the action of tertiary amine on an α-ω dihalogenated alkane giving either a dichloro, dibromo, or dilodo alkane. The reaction can take place without solvents, preferably under nitrogen atmosphere, whenever at least one of the reagents can serve as the solvent medium. The reaction can also be performed in a solvent chosen among alcohols, ketones, dimethylformamide, acetonitrile, ethers, polyglycol ethers, or a mixture of several solvents chosen among the preceding or their mixture in aromatic hydrocarbons such as toluene or benzene. The quaternary ammonium halide, for example dibromide if dibromoalkane is used, is thus isolated.

The proportions for the reagents are determined in accordance with the stoichiometry, but there can be an excess of the halogenated derivative, namely when the halogenated derivative can be used as the reaction solvent.

A salt of another mineral or organic acid can however be obtained by a usual procedure using an ion exchange resin. The reaction can be performed at room temperature, however the temperature will be raised to accelerate the process. This temperature will range between room temperature and the boiling temperature of solvent used.

If a non-symmetrical derivative is to be obtained, an equivalent tertiary amine is reacted with a primary ω-alkanol, then the alcohol group is halogenated using a hydrohalogenic acid, for example concentrated hydrobromic acid, giving an halogenated quaternary ammonium alkyl, which will then be reacted with the chosen second quaternary amine.

The final product can be isolated directly by crystallization from the reaction medium, it can also be separated form the solvent by evaporation and recrystallized in another solvent chosen among alcohols, ketones, esters, ethers, ether-alcohols, acetic acid. These compounds can be administered orally, parenterally, rectally, percutaneously or permucosally, in the form of tablets, enrobed tablets, capsules, solutions, syrups, emulsions, suspensions, or formulations enabling modulated release of the active substance. Such compositions can be administered to humans or animals at doses ranging from 0.01 mg/kg to 50 mg/kg.

For an antibabesiosis application, the pharmaceutical compositions are formulated in accordance with veterinary standards.

DETAILED DESCRIPTION OF THE INVENTION

Besides the preceding dispositions, the invention concerns other dispositions described in the following which refers to examples of implementation of the procedure which is the object of the present invention. These examples are given solely as illustrations of the object of the invention and cannot be considered to limit the invention in any way. All the derivatives have been submitted to elementary analysis, with, compared with the calculated values, a 0.3% maximal tolerance in the results obtained. The melting points were measured in a capillary tube and have not been corrected, the boiling points have not been corrected, the pressure being measured with a Pirani gauge. The infrared spectra were obtained with a Philipps PU 9714 device using NaCl slices for liquids and KBr pellets for the solids. The NMR spectra were recorded on a Brucker WP 200 device in deuterochloroform solution or on a DMSOd6 compared with the reference TMS. Unless specifically stated otherwise, the products were isolated as bromhydrates.

EXAMPLES

I/ Synthesis of Certain Active Molecules

Example 1

—N,N'-dimethyl-N,N'-diethyl-N,N'-dipropyl-1,14 tetradecanediaminium, dibromide 200 ml ethanol, 35.6 g (0.1 mole) are added to -1,14 dibromotetradecane and 11.1 g N-ethyl-N-methyl-1 propanamine. The mixture is refluxed for 8 hours to complete reaction, followed by thin-layer chromatography on a silicium plate in a solvent system such as propanol/pyridine/acetic acid/water. The solution is then evaporated and the residue is recrystallized in a isopropanol/ethyl acetate mixture. The crystalline form of the derivative defined is obtained, M.P.=185/190° C.

The non-commercial α-ω dibromated derivatives can be synthesized by methods including malonic synthesis from a dibromoalkane derivative with four less carbon atoms. For example, as described below, synthesis (a/, b/, c/ and d/) of -1,14-dibromotetradecane from dibromodecane:

a/ Synthesis of the ethyl ester of -2,13-diethoxycarbonyl-1,14-tetradecanedionic acid One atom/gram of sodium (23 g) is disolved in 500 ml anhydrous ethanol, 1.1 mole of diethyl malonate is then added. 0.5 moles of -1,10-dibromodecane are added to the resulting suspension at 30 to 50° C. The mixture is refluxed for several hours then, after distillation and water washings, the raw product is distilled. This gives the pure derivative defined in the title in the form of an oil distilling at 160/170° C. under $10^{-3}$ mbar with a 80% yield.

b/ Synthesis of -1,1,4-tetradecanedicarboxylic acid

All of the product obtained in step a/ described above is saponified in a mixture of 170 g potassium and 200 ml water. The alcohol product is distilled followed by addition of concentrated sulfuric acid to strongly acidify the medium. The mixture is held at boiling until the end of the decarboxylation. When all the $CO_2$ has been removed, the mixture is cooled and extracted with a non-miscible solvent washed to neutrality. The derivative described in the title is obtained by evaporation and recrystallization, M.P.=160° C.

c/ Synthesis of -1,14-tetradecanediol

The product obtained in step b/ is esterified in the presence of excess ethanol and a few milliliters of sulfuric acid brought to boiling. The reaction process can be followed by C.C.M. in the following solvent system: formic acid/ethyl formate/toluene. After evaporaing the excess alcohol and washing with water in the presence of a non-miscible solvent, the ethyl ester of -1,14-tetradecanedioic acid is obtained in the form of a thick oil, boiling point=165° C. under 1 mbar. All of the product is reduced by LiAlH$_4$ in solution in the THF, the reduction is followed by C.C.M. After treating with dilute acid, the product is extracted with a solvent then chromatographed on a silicium column with a hexane/ethyl acetate mixture. Total yield from the diacid is greater than 65%.

d/ Synthesis of -1,14-dibromotetradecane 23 g (0.1 mole) of dialcohol are added to 200 ml 48% bromhydric acid and refluxed for 24 hours. After cooling, the organic phase is separated, redissolved in chloroform, and washed with water. The derivative defined in the title is obtained by chromatography on a silicium column with hexane with a 45% yield from the alcohol, the melting point of this product is 43° C.

The following derivatives are obtained by proceeding as described in example 1, using the corresponding dibromoalkanes instead of-1,14-dibromotetradecane:

Example 2

—N,N'-dimethyl-N,N'-diethyl-N,N'-dipropyl-1,15-pentadecanediaminium dibromide, M.P.=230° C.

Example 3

N,N'-dimethyl-N,N'-diethyl-N,N'-dipropyl-1,16-hexadecanediaminium dibromide, M.P.=232° C.

Example 4

N,N'-dimethyl-N,N'-diethyl-N,N'-dipropyl-1,17-heptadecanediaminium dibromide, M.P.=205° C.

Example 5

N,N'-dimethyl-N,N'-diethyl-N,N'-dipropyl-1,18-octadecanediaminium dibromide, M.P.=175° C.

Example 6

N,N'-dimethyl-N,N'-diethyl-N,N'-dipropyl-1,20-eicosanediaminium dibromide, M.P.=130° C.

Example 7

N,N'-dimethyl-N,N'-diethyl-N N'-dipropyl-1,22-cosanediaminium dibromide, M.P.=130° C.

Example 8

N,N,N,N',N',N'-hexapropyl-1,14-tetradecanediaminium dibromide 3.56 g (10 mM) of -1,14-dibromotetradecane are added to 20 ml tripropylamine and held at 80/90° C. over night. The excess tertiary amine is evaporated under vacuum, and a minimal amount of ethanol is added to redissolve the derivative which is reprecipitated with ether. The derivative defined in the title is obtained by recrystallization in a isopropanol/iisopropylic ether mixture, M.P.=170° C.

Example 9

N,N,N,N',N',N'-hexapropyl-1,16-hexadecanediaminium dibromide.

The hygroscopic form of the derivative defined in the title is obtained by applying the same procedue as described above using -1,16-dibromohexadecane and recrystallizing with methanol/ether, M.P.=185° C.

Example 10

N,N,N,N', N',N'-hexapropyl-1,20-eicosanediaminium dibromide

The malonic synthesis described in example 1 is applied to -1-16-dibromohexadecane to obtain pure -1,20-eicosandiol after column chromatography, M.P.=93° C. Bromation following the prodecure described in example 1-d/-variant 2, produces -1,20-dibromoeicosane, M.P.=62° C. Reaction with tripropylamine according to the procedure described in example 1 produces the crystalline form of the derivative defined in the title, M.P.=205° C.

Example 11

N,N,N,N',N',N'-hexapropyl-1,24-tetracosanediaminium dibromide

In this example, the malonic synthesis uses the bromated derivative described above and produces -1,24-dibromotetracosane, which, when treated with tripropylamine as described in example 1 gives the derivative described in the title, M.P.=105° C.

Example 12

N,N,N,N',N',N'-hexapropyl-1,16-hexadecanediaminium dibromide

The crystalline form of the derivative defined in the title is obtained using the -1,16-dibromohexadecane derivative and tripropylamine according to the conditions described above, M.P. 227° C.

Example 13

N,N'-dimethyl-,N,N,N',N'-tetraethyl-1,16-hexadecanediaminium dibromide

The derivative defined in the title is obtained by replacing tripropylamine with N-methyldiethylamine, M.P.=170° C.

Example 14

N,N'-dimethyl-,N,N,N',N'-tetraethyl-1,18-octadecanediaminium dibromide

Operating as described above with -1,18-dibromooctadecane gives the derivative defined in the title, M.P.=206° C.

Example 15

N,N'-dimethyl-,N,N,N',N'-tetraethyl-1,21-heneicosanediaminium dibromide

Using the corresponding diol obtained according to the method described by Lukes (Col. Czech. Chem. Comm. 26, -1961- 1719/1722) and by action of phosphorus tribromide according to example 1 gives the α-ω dibromated derivative which is reacted with N-methyldiethylamine to produce the derivative defined in the title, M.P.=205° C.

Example 16

-1,1'-(1,14-tetradecanediyl)bis(1-methylpyrrolidium) dibromide 21.36 g (0.06 mole) of -1,14-dibromodecane and 11.07 g (0.13 mole) N-methylpyrrolidine are added to 200 ml ethanol, refluxed for 6 hours until complete reaction. The derivative defined in the title is obtained after evaporation to dry and recrystallization in an ethanol/ether mixture, M.P.= 192° C.

Example 17

-1,1'-(1,16-hexadecanediyl)bis(1-methylpyrrolidium) dibromide

With the conditions of the example given above and with -1,16-dibromodecane, using N-methylpyrrolidine gives the cristalline form of the derivative defined in the title, M.P.= 178° C.

Example 18

-1,1'-(1,14-tetradecanediyl)bis(2-hydroxymethl-1 -methylpyrrolidium) dibromide

If 2-hydroxymethyl-1-methyl-pyrrolidine is substituted for N-methylpyrrolidine in the preceeding example, the derivative defined in the title is obtained, M.P.=95° C.

Example 19

-1,1'-(1,22-docosanediyl)bis(2-hydroxymethl-1 -methylpyrrolidium) dibromide

With 1,22-dibromodocosane, starting with the corresponding dialcohol, iteslf synthesized by the action of bromhydric acid on the docosa-1,21-diene, the derivative defined in the title is obtained, M.P.=102° C.

Example 20

-1,1'-(1,16-hexadecanediyl)bis(1-methyl-3-hydroxymethylpyrrolidium) dibromide

With the conditions given in example 16 and with -1,16-dibromohexadecane and 1-methyl-3-piperidinemethanol, the derivative defined in the title is obtained, M.P.=107° C.

Example 21

-1,1'-(1,16-hexadecanediyl)bis(1-methylmorphofinium) dibromide

Using the same bromate derivative and N-methylmorpholine, the derivative defined in the title is obtained, M.P.=85° C.

Example 22

N,N'-didodecyl-N,N,N',N'-tetramethyl-1,16-hexadecanediaminium dibromide

With N-dimethyllaurylamine using the dibromated derivative given above, the derivative defined in the title is a white product, M.P.=128° C.

Example 23

N,N'-didodecyl-N,N,N',N'-tetramethyl-1,16-octadecanediaminium dibromide

As above with the C18 dibromo derivative, the derivative defined in the title is obtained, M.P.=103° C.

Example 24

N,N'-di(2-propynyl)-N,N,N',N'-tetramethyl-1,14-tetradecandiaminium dibromide

Using N-dimethylpropagylamine under the preceding conditions gives the derivative defined in the title, M.P.= 145° C.; the NMR spectrum recorded with the DMSOd6 shows characteristic chemical shifts: 3.4 ppm (m), 4H, —N—$\underline{CH2}$—CH2—, 4.1 ppm; 4.1 ppm (t), 2H $\underline{CH}$+C—; 4.5 ppm (d) 4H, C—$\underline{CH2}$—N—

Example 25

N,N'-di(2-propenyl)-N,N,N',N'-tetramethyl-1,14-tetradecanediaminium dibromide

As above, with N-dimethylallylamine, the derivative defined in the title is obtained, M.P.=50/60° C. The characteristic NMR chemical shifts are –4.0 ppm (d), 4H, CH—$\underline{CH2}$—N-5.6 ppm (m) 4H, $\underline{CH2}$=CH—; 6.0 ppm (m), CH2=$\underline{CH}$—CH2.

Example 26

N,N'-di(3-butynyl)-N,N,N',N'-tetramethyl-1,14-tetradecanediaminium dibromide

Likewise as above, with the corresponding acetylinic amine, the derivative defined in the title is obtained, M.P.= 170° C. The NMR spectrum has the following chemical shifts: 2.75 ppm (td), 4H, CH2+C—C—$\underline{CH2}$—CH2—N, 3.1 ppm (t) 2H, $\underline{CH}$+C—CH2; 3.25 ppm (m) 4H, CH+C—CH2—$\underline{CH2}$—N—.

Example 27

N,N'-di(2-hydroxyethyl)-N,N,N',N'-tetrapropyl-1,14-tetradecanediaminium dibromide With N-dipropylethanolamine and the C14 bromide derivative, the derivative defined in the title is obtained, M.P.=188/190° C.

Example 28

N,N'-di(2-ethoxyethyl)-N,N,N',N'-tetrapropyl-1,14-tetradecanediaminium dibromide Likewise as above, with N-dipropyl-2-ethoxyethylamine, the derivative defined in the title is obtained, M.P.=145/150° C.

Example 29

N,N'-di-(2- hydroxyethyl)-N,N,N',N'-tetrapropyl-1, 16 hexadecane diaminium dibromide As in example 27, with the -1,16-dibromohexadecane instead of -1,14-tetradecane and the title compound is obtained, M.P.=120° C.

Example 30

N,N'-di(2-hydroxyethyl)-N,N,N',N'-tetrapropyl-1,20-eicosanediaminium dibromide.

By action of the C20 dibromide derivative, as in the preceding example, the derivative defined in the title is obtained, M.P.=85/90° C.

II/ Antimalaria Activity

The antimalaria activity of the derivatives presented in the preceding examples has been tested in humans infested with *Plasmodium falciparum*. The product to test was placed in contact with infected human erythrocytes for 24 hours. A radioactive nucleic acid precursor, ($^3$H) hypoxanthine was then added. The precursor is only incorporated into cells infected with growing parasites, that is in cells which the drug will not have affected.

The capacity to incorporate a precursor or not reflects the viability of the infested cells. The test duration is 60 to 70 hours (DESJARDINS R.E., CANFIELD C. J., HATNES J. D, and CHULAY J. D., Antimicrob. Agents Chemother. 1979, 16, p 710–718). In Table 1, below, the results are expressed as ED50, i.e. the product dose in the experimental medium which inhibits parasite growth in vitro by 50%.

The mechanism of action was verified on the different derivatives defined in the invention by studying the specific interference with the biosynthesis of different biomolecules, nucleic acids, proteins and phospholipids using the incorporation of the radiolabeled precursors ($^3$H)hypoxanthine, ($^3$H) isoleucine, (3H) choline. Specificity phospholipid metabolism was determined by comparison of the effect on ($^3$H) ethanolamine incorporation into phosphatidylethanolamine (Ancelin M. L., Vialettes F. and Vial H. H. 1991, Anal. Biochem. 199, 203–209.

Antimalaria Activity of G25 in the Monkey Infected by Human *P. falciparum* Parasites Besides chimpanzees, only two South American monkey species, Aotus and *Saimiri seirius,* can be infected by *P. falciparum.* Currently, infection of Aotus monkeys with the human parasite is the best, and quasi-unique, model for evaluating therapeutic or vaccinal interventions against malaria (Collins W. E., Gallaud C. G., Sullivan J. S., and Morris C. L., "Selections of different strains of *Plasmodium falciparum* for testing blood stages in *Aotus nancymal* monkeys" An. J. Trop. Med. Hyg., 1994, 51 (2) 224–232).

The antimalaria activity was thus evaluated in the *Aotus lemurinus* monkey infected by the FVO (falciparum Vietnam Oaknoll) isolate of *P. falciparum.* This isolate is chloroquine-resistant and inevitably lethal for Aotus monkeys at the "Fundacion Centro de Primates" at the University del Valle, Cali, Colombia.

Figure 6:
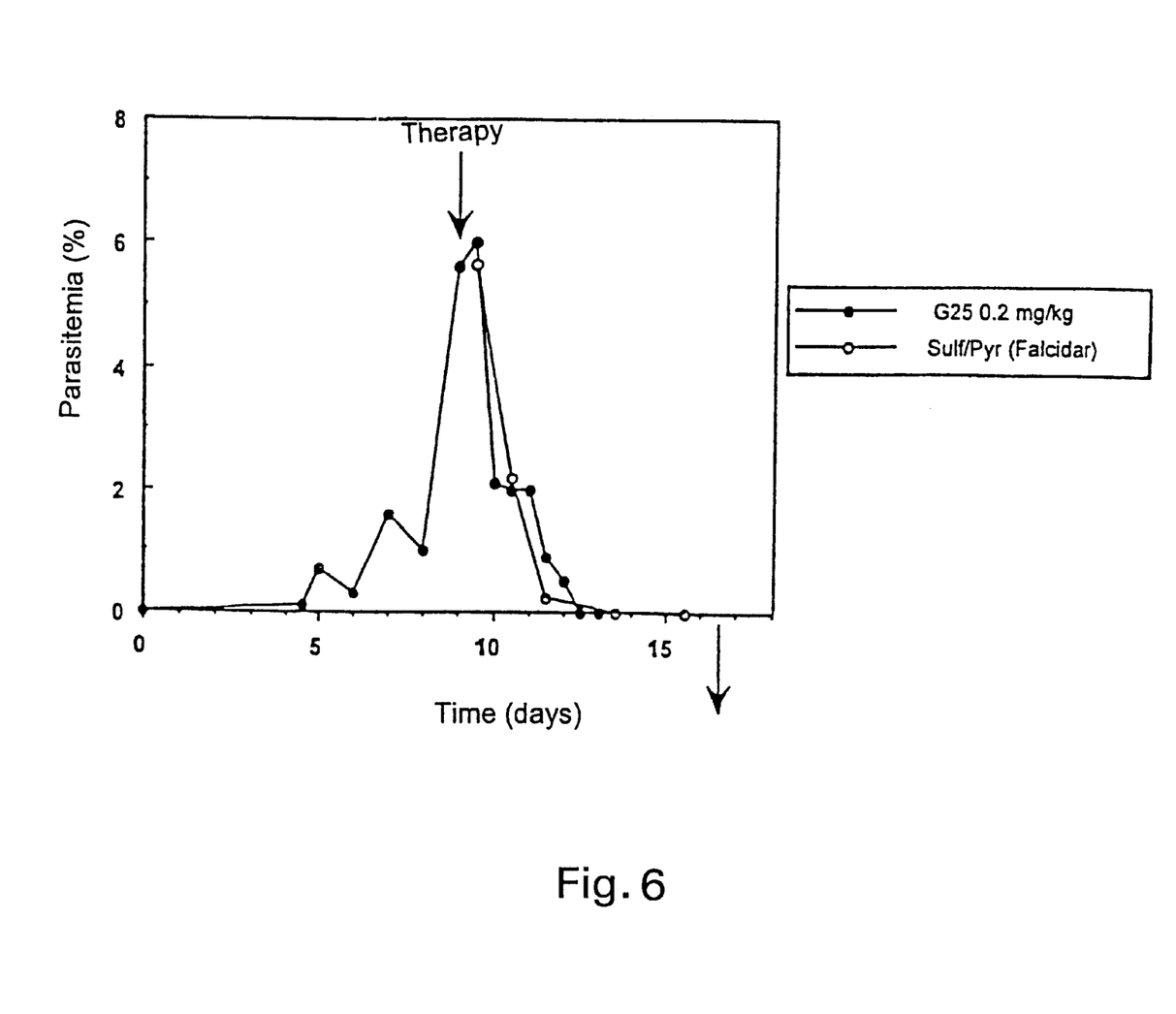
Figure 6: Antimalaria effect of G25 in the monkey infected with P. falciparum with a 6% parasitemia.

As shown in Figure 6, the Aotus monkey was infected by *P. Falciparum* (FVO isolate) on day 0. Treatment with G25 (dissolved in 0.9% NaCl) was initiated when the parasitemia reached 5.6%; 16 doses (0.2 mg/kg b.i.d. for 8 days) were given. The decline in parasitemia was evident at the second dose. The parasitemia in a monkey treated by combination sulfadoxine/pyrimethamine (FANSIDAR) is given for comparison.

In all, 15 monkeys were infected, then treated with G25 given by intramuscular injections at doses ranging from 0.010 to 0.2 mg/kg. Complete cure (validated by PCR) was achieved with no recurrences (the monkeys were followed for 6 months and checked for susceptibility to a new infection) for the doses as low as 0.030 mg/kg. Given at the dose of 0.01 mg/kg, G25 was active (parasite clearance) but did not lead to complete cure (recurrence observed).

Considering that the maximal tolerable dose in the monkey is approximately 1.5 mg/kg, it follows that the therapeutic index ($LD_{50}/ED_{50}$) in the monkey is above 50.

III/ Antimalaria Activity and Toxicity

In order to evaluate the therapeutic index of the different products, the activity of these products was tested in vivo and compared with acute toxicity in animals. This activity was measured using the test described by PETERS W. (Chemotherapy and Drug resistance in Malaria, 1970). A compound was administered for four consecutive days to mice previously infected with *Plasmodium vinckei, petterei* or *chabaudi*. The said compound was dissolved in a 0.9% NaCl solution. The preparations were thus administered intraperitoneally or subcutaneously in male Swiss mice infected by intravenous injection of *Plasmodium petterei* or *Plasmodium chadaudi* ($10^6$ infected cells). The compound was administered twice a day for four consecutive days, the first injection being performed two hours after the infestation and the second, 10 hours later. The parasitemia was determined on blood smears the day after the end of treatment. Toxicity was measured in vivo following the same schedule, the animals having received, under the same administration conditions as above, two injections per day for four days (semi-chronic toxicity). The results are expressed in lethal dose 50 ($LD_{50}$), i.e. the dose causing death in 50% of the animals.

The results of these trials are summarized in Table I, below, and expressed as therapeutic index, or the ratio of activity over toxicity measured under the identical conditions described above.

IV/ Specific Action

1- The molecules of this invention have a specific action on phospholipid metabolism as compared with nucleic acid metabolism, and within phospholipid metabolism. The in vitro activity tests were performed on human erythrocytes infested with *Plasmodium falciparum*. The radiolabeled precursors used, such as choline, ethanolamine or hypoxanthine, were added and enabled measurements of the effect of the product on these different metabolisms. All the compounds tested showed a specific action on the biosynthesis of phosphatidylcholine, with a tight correlation between action on this metabolism and the antimalaria action per se.

2- Inversely, the molecules of this invention have demonstrated a total absence of any action on other cellular systems. Thus their effects on the viability of the SAR lymphoblastoid cell line were measured: there is no correlation between the dose causing a 50% inhibition in the cell line viability LV50 and the effective dose ED50 against *Plasmodium falciparum*. This same ED50 was compared with the ED50 required to inhibit uptake of choline in central nervous system synaptosomes according to the method described by Tamaru (Brain Res. 473, 205–226). The effect on the nervous system is only observed for doses up to 100 to 1000 times higher.

V/ In vitro Antibabesia Activity

The screening process for antimalaria activity, based on parasite incorporation of ($^3$H) hypoxanthine was used to test the antimetabolic activity of such components against *Babesia bovis, Babesia canis.* A tight relationship was found between the rate of ($^3$H) hypoxanthine incorporation using standard measurements and the percentage of parasitized cells determined by microscopy. This metabolic activity was quantified and scored +++ in the table given below for molecules with a test showing a 50% inhibition of ($^3$H) hypoxanthine incorporation (ED50), these molecules having a concentration less than or equal to 0.01 micromoles. The score was ++ for the same activity at a concentration of 0.01 to 0.1 micromoles and finally + for a concentration under or equal to 1 micromole.

TABLE I

| Compound | ED50 expressed in micromoles | Therapeutic index | Antibabesia activity at 10 millimoles |
|---|---|---|---|
| EXAMPLE 1 | 0.01 | 50 | ++ |
| EXAMPLE 2 | 0.01 | 42 | + |
| EXAMPLE 3 | 0.003 | 15 | 22 |

TABLE I-continued

| Compound | ED50 expressed in micromoles | Therapeutic index | Antibabesia activity at 10 millimoles |
|---|---|---|---|
| EXAMPLE 4 | 0.002 | 17 | ++ |
| EXAMPLE 5 | 0.001 | 12 | +++ |
| EXAMPLE 6 | 0.003 | 15 | ++ |
| EXAMPLE 7 | 0.01 | 35 | ++ |
| EXAMPLE 8 | 0.1 | 20 | + |
| EXAMPLE 9 | 0.007 | 36 | +++ |
| EXAMPLE 10 | 0.7 | 14 | + |
| EXAMPLE 11 | 1.6 | 28 | + |
| EXAMPLE 12 | 0.001 | 11 | ++ |
| EXAMPLE 13 | 0.0005 | 6 | +++ |
| EXAMPLE 14 | 0.00004 | 14 | +++ |
| EXAMPLE 15 | 0.000003 | 12 | +++ |
| EXAMPLE 16 | 0.0009 | 8 | +++ |
| EXAMPLE 17 | 0.0006 | 7 | +++ |
| EXAMPLE 18 | 0.001 | 22 | +++ |
| EXAMPLE 19 | 0.07 | 40 | + |
| EXAMPLE 20 | 0.0003 | 17 | +++ |
| EXAMPLE 21 | 0.001 | 25 | +++ |
| EXAMPLE 22 | 1 | 20 | ++ |
| EXAMPLE 23 | 0.1 | 35 | + |
| EXAMPLE 24 | 0.007 | 12 | ++ |
| EXAMPLE 25 | 0.005 | 15 | +++ |
| EXAMPLE 26 | 0.04 | 45 | ++ |
| EXAMPLE 27 | 0.01 | 15 | ++ |
| EXAMPLE 28 | 0.01 | 40 | +++ |
| EXAMPLE 29 | 0,005 | 12 | ++ |
| EXAMPLE 30 | 0,0003 | 55 | +++ |

Figure Legends

What is claimed is:

1. A pharmaceutical composition composed of a physiologically acceptable excipient and, as the active substance, a compound comprising the following general formula (1):

(1)

wherein:
R1 designates a hydrocarbon group with 1 to 20 carbon atoms, and
R2 and R3 are identical or different and independently designate a hydrocarbon group with 1 to 20 carbon atoms having methyl or ethyl substitution groups, or halogen substitution groups wherein said halogen substitution groups are selected from chlorine, bromine and iodine, or trifluoromethyl, trifluoroethyl or trifluoropropyl substitution groups,
where R1 is different from an ethyl group, R2 and R3 are not simultaneously methyl groups, or

R1 designates a hydroxylalkyl group composed of 1 to 5 carbon atoms, where the hydroxyl groups are etherified by a methyl, ethyl group substitution of the hydrogen atom or substituted with silicyl derivatives of —Si(CH$_3$)$_3$, and
R2 and R3 are identical or different and designate a saturated hydrocarbon which is substituted with halogen groups wherein said halogen substitution groups are selected from chlorine, bromine and iodine, or with trifluoromethyl, trifluoroethyl or trifluoropropyl groups, or

R1 designates a mono-or polyunsaturated hydrocarbon with 1 to 6 carbon atoms, and
R2 and R3 are identical or different and designate a straight- or branched-chain alkyl group composed of 1 to 20 hydrocarbon units having methyl or ethyl substitution groups, or halogen substitution groups wherein said halogen substitution groups are selected from chlorine, bromine and iodine, or trifluoromethyl, trifluoroethyl or trifluoropropyl substitution groups, or

R1 designates a hydrocarbon with 1 to 20 carbon atoms, and
R2 and R3 form, together with nitrogen, a saturated heterogeneous cycle composed of 4 to 5 carbon atoms where one of the carbon atoms is replaced by a silicium atom, an oxygen atom or a sulfur atom, this cycle having an alkyl substitution with 1 to 3 carbon atoms which are hydroxylated, halogenated, or silicylated, where R1', R2' and R3' have the same definition as R1, R2 and R3 in the formula (1), without the restriction concerning the methyl and ethyl groups, the two polar heads being identical or not;

and where X designates a hydrocarbon having an alkyl substitution with 1 to 3 carbon atoms, the hydrocarbon chain having 12 to 26 carbon atoms, excluding the following compounds:

2. The pharmaceutical composition according to claim 1, wherein

R1 designates an alkyl group selected from the group of: methyl, methylethyl, propyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl and eicosyl, and R2 and R3 are identical or different and independently designate an alkyl group selected from the group of: ethyl, propyl, isopropyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl and eicosyl which have methyl or ethyl substitution groups, or halogen substitution groups wherein said halogen substitution groups are selected from chlorine, bromine and iodine, or trifluoromethyl, trifluoroethyl or trifluoropropyl substitution groups.

3. The pharmaceutical composition according to claim 1, wherein:

R1 is a hydroxyalkyl group composed of 1 to 5 carbon atoms selected from the group of hydroxymethyl, hydroxyethyl, hydroxypropyl and hydroxypentyl groups, where these hydroxylated groups are etherified by substitution of a methyl, ethyl, or —Si—(CH$_3$)$_3$ group for the hydrogen atom, and R2 and R3 are identical or different and are selected from the group of a saturated propyl, isopropyl, butyl, sec-butyl, tert-butyl, pently, hexyl, heptyl, octyl, nonyl, decyl, undecyl and dodecyl hydrocarbon which have halogen substitution groups wherein said halogen substitution groups are selected from chlorine, bromine and iodine, or trifluoromethyl, trifluoroethyl or trifluoropropyl substitution groups.

4. The pharmaceutical composition according to claim 1, wherein:

R1 designates a mono- or polyunsaturated hydrocarbon chain selected from the group of propenyl, propynyl, butenyl, butynyl, butadienyl, pentenyl, pentadienyl, pentynyl, hexenyl, hexadienyl, hexynyl and isoprenyl, and R2 and R3 are identical or different and designate a straight- or branched-chain alkyl composed of 1 to 20 hydrocarbon units selected from the group of methyl, ethyl, propyl, isopropyl, butyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl which have halogen substitution groups wherein said halogen substitution groups are selected from chlorine, bromine and iodine, or trifluoromethyl, trifluoroethyl or trifluoropropyl substitution groups.

5. The pharmaceutical composition according to claim 1, wherein:

R1 designates a methyl, methylethyl, propyl, butyl, sec-butyl, tert-butyl, pently, hexyl, heptyl, octyl, nonyl, decyl, undecyl, dodecyl, tridecyl, tetradecyl, pentadecyl, hexadecyl, heptadecyl, octadecyl, nonadecyl, eicosyl group, and R2 and R3 form, together with nitrogen, a saturated heterogeneous cycle composed of 4 to 5 carbon atoms where one of the carbon atoms is replaced by a silicium atom, an oxygen atom or a sulfur atom, this cycle having a methyl, ethyl, hydroxymethyl, hydroxyethyl, methyl ethyl or hydroxypropyl substitution, or a trifluoromethyl or trifluoroethyl substitution, or a trimethylsilicyl or trimethylsilicyloxy substitution.

6. The pharmaceutical composition according to claim 1 wherein X designates a straight-chain saturated hydrocarbon having 14 to 26 carbon atoms.

7. The pharmaceutical composition according to claim 1 wherein the active substance is selected from the group of the following compounds:

N,N'-dimethyl-N,N'-diethyl-N,N'-dipropyl-1-20-eicosandediaminium dibromide;
N,N'-dimethyl-N,N'-diethyl-N,N'-dipropyl-1-18-octadecanediaminium dibromide;
N,N'-dimethyl-N,N'-diethyl-N,N'-dipropyl-1-21-heneicosanediaminium dibromide;
-1,1'-(1,14-tetradecaediyl)bis(1-methylpyrrolidinium) dibromide;
-1-1'-(1,16-hexadecanediyl)bis(2-hydroxymethyl-1-methylpyrrolidinium dibromide; and
N,N'-di-(2-hydroxyethyl)-N,N,N',N'-tetrapropyl-1,20-eicosanediaminium dibromide.

8. The pharmaceutical composition according to claim 1, wherein the two polar heads are identical.

9. A method for treating malaria or babesiosis in a mammal said method comprising the step of administering to a mammal in need of such treatment a composition comprising the following general formula:

(1)

wherein:

R1 designates a hydrocarbon group with 1 to 20 carbon atoms, and

R2 and R3 are identical or different and independently designate a hydrocarbon group with 1 to 20 carbon atoms having methyl or ethyl substitution groups, or halogen substitution groups wherein said halogen substitution groups are selected from chlorine, bromine and iodine, or trifluoromethyl, trifluoroethyl or trifluoropropyl substitution groups, where R1 is different from an ethyl group, R2 and R3 are not simultaneously methyl groups, or R1 designates a hydroxylalkyl group composed of 1 to 5 carbon atoms, where the hydroxyl groups are etherified by a methyl, ethyl group substitution of the hydrogen atom or substituted with silicyl derivatives of —Si(CH$_3$)$_3$, and R2 and R3 are identical or different and designate a saturated hydrocarbon which is substituted with halogen groups wherein said halogen substitution groups are selected from chlorine, bromine and iodine, or with trifluoromethyl, trifluoroethyl or trifluoropropyl groups, or R1 designates a mono-or polyunsaturated hydrocarbon with 1 to 6 carbon atoms, and R2 and R3 are identical or different and designate a straight- or branched-chain alkyl group composed of 1 to 20 hydrocarbon units having methyl or ethyl substitution groups, or halogen substitution groups wherein said halogen substitution groups are selected from chlorine, bromine and iodine, or trifluoromethyl, trifluoroethyl or trifluoropropyl substitution groups, or

R1 designates a hydrocarbon with 1 to 20 carbon atoms, and

R2 and R3 form, together with nitrogen, a saturated heterogeneous cycle composed of 4 to 5 carbon atoms where one of the carbon atoms is replaced by a silicium atom, an oxygen atom or a sulfur atom, this cycle having an alkyl substitution with 1 to 3 carbon atoms which are hydroxylated, halogenated, or silicylated, where R1', R2' and R3' have the same definition as R1, R2 and R3 in the formula (1), without the restriction concerning the methyl and ethyl groups, the two polar heads being identical or not;

and where X designates a hydrocarbon having an alkyl substitution with 1 to 3 carbon atoms, the hydrocarbon chain having 12 to 26 carbon atoms.

10. A compound comprising the formula:

11. A process for preparing a pharmaceutical composition comprising the steps of combining an active substance defined by the general formula (1) in accordance with claim 1 with an acceptable physiological excipient.

12. The process according to claim 11 further comprising the step of adding an additive, a preservative, an antioxidant agent or a diluent.

13. The pharmaceutical composition according to claim 1 wherein X designates a straight-chain saturated hydrocarbon having 14 to 22 carbon atoms.

14. The pharmaceutical composition according to claim 1 wherein X designates a straight-chain saturated hydrocarbon having 16 carbon atoms.

15. A pharmaceutical composition composed of a physiologically acceptable excipient and, as the active substance, a compound comprising the following general formula (1):

wherein:
R1 designates a hydrocarbon group with 1 to 20 carbon atoms, and
R2 and R3 are identical or different and independently designate a hydrocarbon group with 1 to 20 carbon atoms, where R1 is different from an ethyl group, R2 and R3 are not simultaneously methyl groups
where R1', R2' and R3' have the same definition as R1, R2 and R3 in the formula (1), without the restriction concerning the methyl and ethyl groups, the two polar heads being identical or not;
and where X designates a hydrocarbon having 12 to 26 carbon atoms, excluding the following compounds:

16. The pharmaceutical composition according to claim 15, wherein R2 and R3 are identical or different and independently designate a hydrocarbon group with 1 to 20 carbon atoms having methyl or ethyl substitution groups, or halogen substitution groups or trifluoromethyl, trifluoroethyl or trifluoropropyl substitution groups.

17. The pharmaceutical composition according to claim 16 wherein said halogen substitution groups are selected from chlorine, bromine and iodine.

18. A pharmaceutical composition composed of a physiologically acceptable excipient and, as the active substance, a compound comprising the following general formula (1):

wherein:
R1 designates a hydroxylalkyl group composed of 1 to 5 carbon atoms, and
R2 and R3 are identical or different from each other and designate a saturated hydrocarbon
where R1', R2' and R3' have the same definition as R1, R2 and R3 in the formula (1), without the restriction concerning the methyl and ethyl groups, the two polar heads being identical or not;
and where X designates a hydrocarbon having 12 to 26 carbon atoms, excluding the following compounds:

19. The pharmaceutical composition according to claim 18, wherein said hydroxyalkyl group composed of 1 to 5 carbon atoms has hydroxyl groups that are etherified by a methyl, ethyl group substitution of the hydrogen atom or substituted with silicyl derivatives of $Si(CH_3)_3$.

20. The pharamceutical composition according to claim 18, wherein said saturated hydrocarbon is substituted with halogen groups wherein said halogen substitution groups are selected from chlorine, bromine, iodine, trifluoromethyl, trifluoroethyl and trifluoropropyl groups.

21. A pharmaceutical composition composed of a physiologically acceptable excipient and, as the active substance, a compound comprising the following general formula (1):

wherein:
R1 designates a mono-or polyunsaturated hydrocarbon with 1 to 6 carbon atoms, and
R2 and R3 are identical or different and designate a straight- or branched-chain alkyl group composed of 1 to 20 hydrocarbon units,
where R1', R2' and R3' have the same definition as R1, R2 and R3 in the formula (1), without the restriction concerning the methyl and ethyl groups, the two polar heads being identical or not;

and where X designates a hydrocarbon having 12 to 26 carbon atoms, excluding the following compounds:

22. The pharmaceutical composition according to claim 21, wherein said 1 to 20 hydrocarbon units have methyl or ethyl substitution groups, or halogen substitution groups wherein said halogen substitution groups are selected from chlorine, bromine and iodine, or trifluoromethyl, trifluoroethyl or trifluoropropyl substitution groups.

23. A pharmaceutical composition composed of a physiologically acceptable excipient and, as the active substance, a compound comprising the following general formula (1):

wherein

R1 designates a hydrocarbon with 1 to 20 carbon atoms, and

R2 and R3 form, together with nitrogen, a saturated heterogeneous cycle composed of 4 to 5 carbon atoms where R1', R2' and R3' have the same definition as R1, R2 and R3 in the formula (1), without the restriction concerning the methyl and ethyl groups, the two polar heads being identical or not;

and where X designates a hydrocarbon having 12 to 26 carbon atoms, excluding the following compounds:

24. The pharmaceutical composition according to claim 23, wherein one of the carbon atoms is replaced by a silicium atom, an oxygen atom or a sulfur atom.

25. The pharmaceutical composition according to claim 23, wherein said saturated heterogenous cycle has an alkyl substitution with 1 to 3 carbon atoms which are hydroxylated, halogenated, or silicylated.

* * * * *